(12) United States Patent
Choi et al.

(10) Patent No.: US 11,028,119 B2
(45) Date of Patent: *Jun. 8, 2021

(54) SYNTHETIC ROUTE TO 2'-DEOXY-2',2'-DIFLUOROTETRA HYDROURIDINES

(71) Applicant: Otsuka Pharmaceutical Co., Ltd., Tokyo (JP)

(72) Inventors: Hyeong-wook Choi, Andover, MA (US); Steven Mathieu, Windham, NH (US); Frank Fang, Andover, MA (US); Bryan Matthew Lewis, North Brunswick, NJ (US)

(73) Assignee: OTSUKA PHARMACEUTICAL CO., LTD., Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 16/717,811

(22) Filed: Dec. 17, 2019

(65) Prior Publication Data

US 2020/0123189 A1 Apr. 23, 2020

Related U.S. Application Data

(63) Continuation of application No. 15/813,743, filed on Nov. 15, 2017, now Pat. No. 10,526,362, which is a continuation of application No. 15/027,022, filed as application No. PCT/US2014/062874 on Oct. 29, 2014, now Pat. No. 9,834,576.

(60) Provisional application No. 61/896,703, filed on Oct. 29, 2013.

(51) Int. Cl.
| | |
|---|---|
| *C07H 19/00* | (2006.01) |
| *C07H 19/06* | (2006.01) |
| *C07H 1/00* | (2006.01) |
| *C07H 19/04* | (2006.01) |
| *C07B 57/00* | (2006.01) |
| *C07H 1/06* | (2006.01) |
| *C07H 17/02* | (2006.01) |

(52) U.S. Cl.
CPC ............ *C07H 19/06* (2013.01); *C07B 57/00* (2013.01); *C07H 1/00* (2013.01); *C07H 1/06* (2013.01); *C07H 19/04* (2013.01); *C07B 2200/07* (2013.01); *C07H 17/02* (2013.01)

(58) Field of Classification Search
None
See application file for complete search history.

(56) References Cited

U.S. PATENT DOCUMENTS

| | | | |
|---|---|---|---|
| 4,526,988 | A | 7/1985 | Hertel |
| 5,371,210 | A | 12/1994 | Chou |
| 5,521,294 | A | 5/1996 | Wildfeuer |
| 5,552,539 | A | 9/1996 | Duplaa et al. |
| 5,932,719 | A | 8/1999 | Abushanab et al. |
| 5,945,547 | A | 8/1999 | Chou et al. |
| 6,001,994 | A | 12/1999 | Weigel |
| 6,136,791 | A | 10/2000 | Nyce |
| 6,326,491 | B1 | 12/2001 | Abushanab et al. |
| 7,125,983 | B2 | 10/2006 | Iizuka et al. |
| 8,268,800 | B2 | 9/2012 | Hamilton et al. |
| 9,834,576 | B2 | 12/2017 | Choi et al. |
| 10,526,362 | B2 | 1/2020 | Choi et al. |
| 2004/0063926 | A1 | 4/2004 | Iizuka et al. |
| 2009/0137521 | A1 | 5/2009 | Hamilton et al. |

FOREIGN PATENT DOCUMENTS

| | | |
|---|---|---|
| AU | 728377 | 1/2001 |
| CN | 101827856 | 9/2010 |
| EA | 014909 | 2/2011 |
| EP | 1343712 | 10/2003 |
| JP | 2011500713 | 1/2011 |
| WO | 2007/149891 | 12/2007 |
| WO | 2009/052287 | 4/2009 |

OTHER PUBLICATIONS

Sidorov et al. Radiochemistry (2002), vol. 44, No. 3, pp. 295-297.*
Examination Report corresponding to Australian Application No. 2014342402 dated Dec. 13, 2017 (3 pages).
Examination Report corresponding to European Application No. 14802970.5 dated Dec. 12, 2017 (5 pages).
Examination Reporting to European Application No. 14802970.5 dated Feb. 14, 2017 (5 pages).
Examination Report corresponding to European Application No. 14802970.5 dated Jun. 29, 2017 (5 pages).
Ferraris et al. "Design, Synthesis, and Pharmacological Evaluation of Fluorinated Tetranydrouridine Derivatives as Inhibitors of Cytidine Deaminase", J. Med. Chem. 57:2582-2588 (2014).
First Examination Report corresponding to New Zealand Application No. 718607 dated Nov. 30, 2018.
Fujiwara et al. "First-principles and direct design approaches for the control of pharmaceutical crystallization", Journal Process Control 15:493-504 (2005).
Kim et al. "Synthesis of Pyrimidin-2-one Nucleosides as Acid-Stable Inhibitors of Cytidine Deaminase", J. Med. Chem. 29:1374-1380 (1986).

(Continued)

*Primary Examiner* — Patrick T Lewis
(74) *Attorney, Agent, or Firm* — Myers Bigel, P.A.

(57) ABSTRACT

The present invention relates to methods and intermediates for synthesizing 2'-deoxy-2',2'-difluorotetrahydrouridine compounds.

12 Claims, No Drawings

(56) References Cited

OTHER PUBLICATIONS

Norton et al., "Synthesis of Deoxytetrahydrouridine", J. Org. Chem. 74:2221-2221 (2009).
Notification Concerning Transmittal of International Preliminary Report on Patentability corresponding to International Application No. PCT/US2014/062874 dated May 12, 2016.
Notification of Transmittal of the International Search Report and the Written Opinion of the International Searching Authority, or the Declaration corresponding to International Application No. PCT/US2014/062874 dated Jan. 19, 2015.
Office Action corresponding to Chinese Application No. 201480059455.9 dated Jan. 30, 2018.
Office Action corresponding to Indian Application No. 201617012649 dated Feb. 21, 2019.
Office Action corresponding to Indonesian Application No. P00201603488 dated May 23, 2019.
Office Action corresponding to Israeli Application No. 244849 dated Jul. 19, 2018.
Office Action corresponding to Japanese Application No. 2016-526889 dated Jul. 13, 2018.
Office Action corresponding to Mexican Application No. MX/a/2016/005596 dated Sep. 11, 2018.
Office Action corresponding to Philippine Application No. 1-2016-500683 dated Jun. 26, 2019.
Office Action corresponding to Russian Application No. 2016115523 dated Jun. 5, 2018.
Second Examination Report corresponding to New Zealand Application No. 718607 dated May 3, 2019.
U.S. Appl. No. 15/027,022, filed Oct. 29, 2014; Office Action dated May 2, 2017.
"Office Action corresponding to Chinese Application No. 201480059455.9 dated Aug. 23, 2018".
"Office Action corresponding to Malaysian Application No. PI2016701546 dated Nov. 26, 2019".
"Office Action corresponding to New Zealand Application No. 718607 dated Sep. 6, 2019".
"Office Action corresponding to Philippine Application No. 1-2016-500683 dated Oct. 2, 2019".
"Office Action corresponding to Russian Application No. 2016115523 dated Sep. 19, 2018".
"Office Action corresponding to Vietnamese Application No. 1-2016-01406 dated May 28, 2020".

\* cited by examiner

SYNTHETIC ROUTE TO 2'-DEOXY-2',2'-DIFLUOROTETRAHYDROURIDINES

STATEMENT OF PRIORITY

This application is a continuation application of and claims priority to U.S. patent application Ser. No. 15/813,743, filed Nov. 15, 2017, now allowed, which is a continuation application of and claims priority to U.S. patent application Ser. No. 15/027,022, filed Apr. 4, 2016, now U.S. Pat. No. 9,834,576, which is a 35 U.S.C. § 371 national phase application of PCT Application PCT/US2014/062874, filed Oct. 29, 2014 which claims the benefit of U.S. Provisional Application Ser. No. 61/896,703, filed Oct. 29, 2013, the entire contents of which are incorporated by reference herein.

FIELD OF THE INVENTION

The present invention relates to methods and intermediates for synthesizing 2'-deoxy-2',2'-difluorotetrahydrouridine compounds.

BACKGROUND

Several important chemotherapeutic compounds are analogs of the nucleotide cytidine, including decitabine, gemcitabine, 5-azacytidine, ara-C, tezacitabine, 5-fluoro-2'-deoxycytidine, and cytochlor. As analogs of cytidine, the compounds are subject to degradation by the enzyme cytidine deaminase (CDA) which degrades the compounds into inactive metabolites. The presence of CDA limits the effectiveness of the cytidine analogs, requiring the administration of higher and/or more frequent doses of the analogs to achieve therapeutic benefit.

One approach to overcoming this problem is to co-administer a CDA inhibitor with the cytidine analog, thereby blocking degradation of the analog. One class of CDA inhibitor is 2'-deoxy-2',2'-difluorotetrahydrouridine compounds. U.S. Pat. No. 8,268,800, incorporated herein by reference in its entirety, discloses compounds in this class, including compound 1:

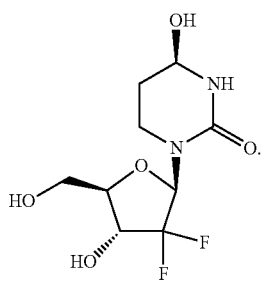

1

A need exists for more efficient processes for producing CDA inhibitors such as 2'-deoxy-2',2'-difluorotetrahydrouridine for use in methods of treating cancer and other disorders.

SUMMARY OF EMBODIMENTS OF THE INVENTION

The present invention relates to the development of a more efficient method for synthesizing 2'-deoxy-2',2'-difluorotetrahydrouridine compounds and intermediates involved in the synthesis. Previous synthetic methods were inconvenient due to the requirement for high pressure hydrogenation and the use of preparative HPLC to isolate the final compound. The improved efficiency of the present method may be achieved as a result of any of the following aspects: (i) it reduces the number of impurities in the final compound, which means that (ii) the final compound can be purified by precipitation or crystallization, e.g., crystallization-induced diastereoselective transformation (CIDT) which converts the mixture of epimers to the desired compound and hence (iii) results in enhanced yield of the desired epimer.

Thus, one aspect of the invention relates to a compound of Formula I:

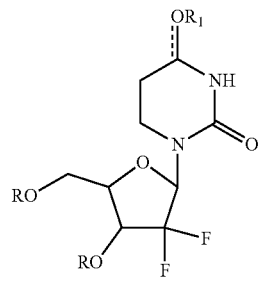

I wherein R is a hydroxyl protecting group;
$R_1$ is H, a hydroxyl protecting group, or absent;
------ is a bond or absent; and
------ is absent when $R_1$ is H or a hydroxyl protecting group;
or a salt, or enantiomer, or diastereomer thereof.

In some embodiments, the compound of Formula I has the structure of Formula II:

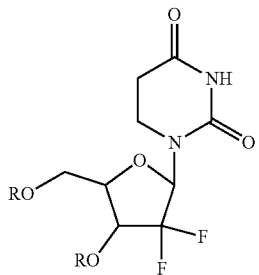

II or a salt, or enantiomer, or diastereomer thereof.

In some embodiments, the compound of Formula I has the structure of Formula III:

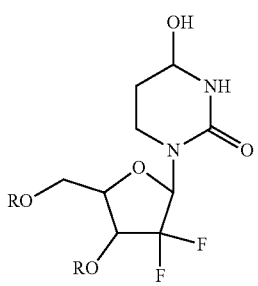

or a salt, or enantiomer, or diastereomer thereof.

A further aspect of the invention relates to a method of producing compound 1 (named (4R)-1-[(2R,4R,5R)-3,3-difluoro-4-hydroxy-5-(hydroxymethyl)tetrahydrofuran-2-yl]-4-hydroxytetrahydropyrimidin-2(1H)-one)):

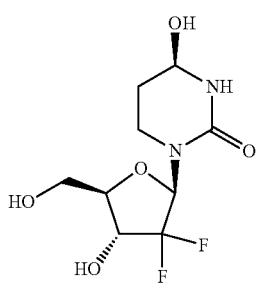

or a salt thereof;

comprising precipitating or crystallizing compound 1 from a solution of compound 2:

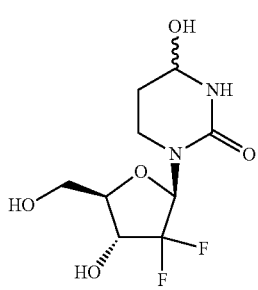

Another aspect of the invention relates to a method of producing compound 1:

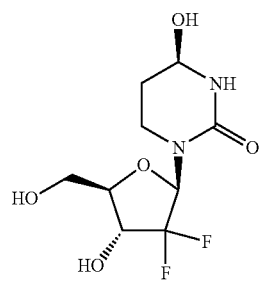

or a salt thereof;
comprising the steps of:
(a) hydrogenating the starting compound of Formula IV:

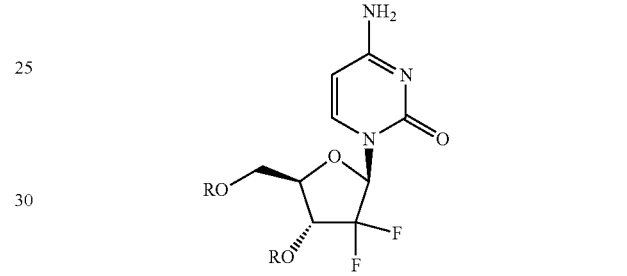

wherein R is a hydroxyl protecting group,
to produce the compound of Formula IIa:

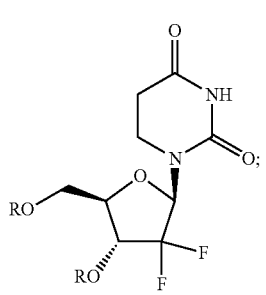

(b) reducing the compound of Formula IIa to produce the compound of Formula IIIa:

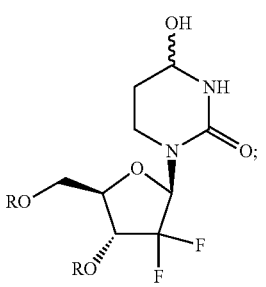

in the presence of a catalyst.

(c) deprotecting the compound of Formula IIIa to produce compound 2:

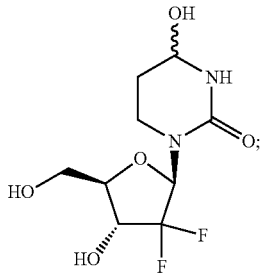

and (d) precipitating or crystallizing compound 2 in the presence of a catalyst to produce compound 1:

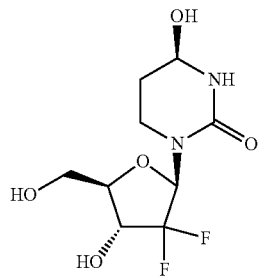

or a salt thereof.

A further aspect of the invention relates to high purity compound 1 (for example compound 1 having a purity of at least about 80%, e.g., at least about 85%, 90%, 95%, 96%, 97%, 98%, 99%, 99.5%, or 99.9%):

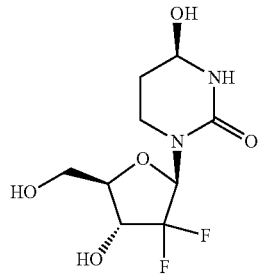

or a salt thereof; produced by the methods of the invention.

DETAILED DESCRIPTION OF EMBODIMENTS OF THE INVENTION

The present invention now will be described hereinafter with reference to the accompanying examples, in which embodiments of the invention are shown. This invention may, however, be embodied in many different forms and should not be construed as limited to the embodiments set forth herein.

Unless otherwise defined, all technical and scientific terms used herein have the same meaning as commonly understood by one of ordinary skill in the art to which this invention belongs. The terminology used in the description of the invention herein is for the purpose of describing particular embodiments only and is not intended to be limiting of the invention.

Unless the context indicates otherwise, it is specifically intended that the various features of the invention described herein can be used in any combination. Moreover, the present invention also contemplates that in some embodiments of the invention, any feature or combination of features set forth herein can be excluded or omitted. To illustrate, if the specification states that a composition comprises components A, B and C, it is specifically intended that any of A, B or C, or a combination thereof, can be omitted and disclaimed singularly or in any combination.

For purposes herein, if there is any ambiguity as between a written chemical name and a drawn chemical structure, the drawn chemical structure will control.

Definitions

As used herein, "a," "an," or "the" can mean one or more than one. For example, "a" compound can mean a single compound or a multiplicity of compounds.

Also as used herein, "and/or" refers to and encompasses any and all possible combinations of one or more of the associated listed items, as well as the lack of combinations when interpreted in the alternative ("or").

The term "about," as used herein when referring to a measurable value such as an amount of dose (e.g., an amount of a compound) and the like, is meant to encompass variations of ±20%, ±10%, ±5%, ±1%, ±0.5%, or even ±0.1% of the specified amount.

The terms "comprise," "comprises," and "comprising" as used herein, specify the presence of the stated features, integers, steps, operations, elements, and/or components, but do not preclude the presence or addition of one or more other features, integers, steps, operations, elements, components, and/or groups thereof.

As used herein, the transitional phrase "consisting essentially of" means that the scope of a claim is to be interpreted to encompass the specified materials or steps recited in the claim "and those that do not materially affect the basic and novel characteristic(s)" of the claimed invention. See, In re Herz, 537 F.2d 549, 551-52, 190 U.S.P.Q. 461, 463 (CCPA 1976) (emphasis in the original); see also MPEP § 2111.03. Thus, the term "consisting essentially of" when used in a claim or the description of this invention is not intended to be interpreted to be equivalent to "comprising."

As used herein, the terms "increase," "increases," "increased," "increasing," and similar terms indicate an elevation of at least about 25%, 50%, 75%, 100%, 150%, 200%, 300%, 400%, 500% or more.

As used herein, the terms "reduce," "reduces," "reduced," "reduction," and similar terms mean a decrease of at least about 5%, 10%, 15%, 20%, 25%, 35%, 50%, 75%, 80%, 85%, 90%, 95%, 97% or more. In particular embodiments, the reduction results in no or essentially no (i.e., an insignificant amount, e.g., less than about 10% or even 5%) detectable activity or amount.

The term "salt thereof" includes pharmaceutically acceptable salts. The term "pharmaceutically acceptable salts" shall mean non-toxic salts of the compounds employed in this invention which are generally prepared by reacting the free acid with a suitable organic or inorganic base or the free base with a suitable organic or inorganic acid. Examples of such salts include, but are not limited to, acetate, benzenesulfonate, benzoate, bicarbonate, bisulfate, bitartrate, borate, bromide, calcium, calcium edetate, camsylate, carbonate, chloride, clavulanate, citrate, dihydrochloride, edetate, edisylate, estolate, esylate, fumarate, gluceptate, gluconate, glutamate, glycollylarsanilate, hexylresorcinate, hydrabamine, hydrobromide, hydrochloride, hydroxynapthoate, iodide, isothionate, lactate, lactobionate, laurate, malate, maleate, mandelate, mesylate, methylbromide, methylnitrate, methylsulfate, mucate, napsylate, nitrate, oleate, oxalate, pamoate, palmitate, panthothenate, phosphate/diphosphate, polygalacturonate, potassium, salicylate, sodium, stearate, subacetate, succinate, tannate, tartrate, teoclate, tosylate, triethiodide, and valerate.

The term "Bronsted-Lowry base" as used herein refers to a species with the ability to accept a proton.

The term "hydroxyl protecting group" as used herein may be any suitable hydroxyl protecting group, i.e., a labile chemical moiety which is known in the art to protect a hydroxyl group against undesired reactions during synthetic procedures. After said synthetic procedure(s) the blocking group as described herein may be selectively removed. See, e.g., A. Isidro-Llobet et al., Amino Acid-Protecting Groups, Chem. Rev. 109:2455-2504 (2009) and T. Greene and P. Wuts, *Protective Groups in Organic Synthesis* (3d Ed. 1999). In some embodiments, the hydroxyl protecting group is an acid-stabile hydroxyl protecting group. Examples of hydroxyl protecting groups include, but are not limited to, alkyl, cycloalkyl, arylalkyl, aryl, ethers, esters, cyclic ethers, cyclic esters, acetal, cyclic acetal, ketal, and cyclic ketal groups and the like that can be removed under either acidic or basic conditions so that the protecting group is removed and replaced with a hydrogen atom. Specific hydroxyl protecting groups include, but are not limited to, methyl, ethyl, acetate, ethylacetate, propionate, ethylene glycol, propylene glycol, 4-methoxybenzyl, benzyl, trityl, trimethylsilyl, tetrahydropyranyl, and benzoyl. Other hydroxyl protecting groups include, but are not limited to, methoxylmethyl (MOM), methylthiomethyl (MTM), t-butylthiomethyl, (phenyldimethylsilyl)methoxymethyl (SMOM), benzyloxymethyl (BOM), p-methoxybenzyloxymethyl (PMBM), (4-methoxyphenoxy)methyl (p-AOM), guaiacolmethyl (GUM), t-butoxymethyl, 4-pentenyloxymethyl (POM), siloxymethyl, 2-methoxyethoxymethyl (MEM), 2,2,2-trichloroethoxymethyl, bis(2-chloroethoxy)methyl, 2-(trimethyl silyl)ethoxymethyl (SEMOR), tetrahydropyranyl (THP), 3-bromotetrahydropyranyl, tetrahydrothiopyranyl, 1-methoxycyclohexyl, 4-methoxytetrahydropyranyl (MTHP), 4-methoxytetrahydrothiopyranyl, 4-methoxytetrahydrothiopyranyl S,S-dioxide, 1-[(2-chloro-4-methyl)phenyl]-4-methoxypiperidin-4-yl (CTMP), 1,4-dioxan-2-yl, tetrahydrofuranyl, tetrahydrothiofuranyl, 2,3,3a,4,5,6,7,7a-octahydro-7,8,8-trimethyl-4,7-methanobenzofuran-2-yl, 1-ethoxyethyl, 1-(2-chloroethoxy)ethyl, 1-methyl-1-methoxyethyl, 1-methyl-1-benzyloxyethyl, 1-methyl-1-benzyloxy-2-fluoroethyl, 2,2,2-trichloroethyl, 2-trimethyl silylethyl, 2-(phenylselenyl)ethyl, t-butyl, allyl, p-chlorophenyl, p-methoxyphenyl, 2,4-dinitrophenyl, benzyl, p-methoxybenzyl, 3,4-dimethoxybenzyl, o-nitrobenzyl, p-nitrobenzyl, p-halobenzyl, 2,6-dichlorobenzyl, p-cyanobenzyl, p-phenylbenzyl, 2-picolyl, 4-picolyl, 3-methyl-2-picolyl N-oxide, diphenylmethyl, p,p'-dinitrobenzhydryl, 5-dibenzosuberyl, triphenylmethyl, α-naphthyldiphenylmethyl, p-methoxyphenyldiphenylmethyl, di(p-methoxyphenyl)phenylmethyl, tri(p-methoxyphenyl)methyl, 4-(4'-bromophenacyloxyphenyl)diphenylmethyl, 4,4',4''-tris(4,5-dichlorophthalimidophenyl)methyl, 4,4',4''-tris(levulinoyloxyphenyl)methyl, 4,4',4''-tris(benzoyloxyphenyl)methyl, 3-(imidazol-1-yl)bis (4',4''-dimethoxyphenyl)methyl, 1,1-bis(4-methoxyphenyl)-1'-pyrenylmethyl, 9-anthryl, 9-(9-phenyl)xanthenyl, 9-(9-phenyl-10-oxo)anthryl, 1,3-benzodithiolan-2-yl, benzisothiazolyl S,S-dioxido, trimethylsilyl (TMS), triethylsilyl (TES), triisopropylsilyl (TIPS), dimethylisopropylsilyl (IPDMS), diethylisopropylsilyl (DEIPS), dimethylthexylsilyl, t-butyldimethylsilyl (TBDMS), t-butyldiphenylsilyl (TBDPS), tribenzylsilyl, tri-p-xylylsilyl, triphenylsilyl, diphenylmethylsilyl (DPMS), t-butylmethoxyphenylsilyl (TBMPS), formate, benzoylformate, acetate, chloroacetate, dichloroacetate, trichloroacetate, trifluoroacetate, methoxyacetate, triphenylmethoxyacetate, phenoxyacetate, p-chlorophenoxyacetate, 3-phenylpropionate, 4-oxopentanoate (levulinate), 4,4-(ethylenedithio)pentanoate (levulinoyldithioacetal), pivaloate, adamantoate, crotonate, 4-methoxycrotonate, benzoate, p-phenylbenzoate, 2,4,6-trimethylbenzoate(mesitoate), alkyl methyl carbonate, 9-fluorenylmethyl carbonate (Fmoc), alkyl ethyl carbonate, alkyl 2,2,2-trichloroethyl carbonate (Troc), 2-(trimethylsilyl)ethyl carbonate (TMSEC), 2-(phenylsulfonyl)ethyl carbonate (Psec); 2-(triphenylphosphonio)ethyl carbonate (Peoc), alkyl isobutyl carbonate, alkyl vinyl carbonate alkyl allyl carbonate, alkyl p-nitrophenyl carbonate, alkyl benzyl carbonate, alkyl p-methoxybenzyl carbonate, alkyl 3,4-dimethoxybenzyl carbonate, alkyl o-nitrobenzyl carbonate, alkyl p-nitrobenzyl carbonate, alkyl S-benzyl thiocarbonate, 4-ethoxy-1-napthtyl carbonate, methyl dithiocarbonate, 2-iodobenzoate, 4-azidobutyrate, 4-nitro-4-methylpentanoate, o-(dibromomethyl)benzoate, 2-formylbenzenesulfonate, 2-(methylthiomethoxy)ethyl, 4-(methylthiomethoxy)butyrate, 2-(methylthiomethoxymethyl)benzoate, 2,6-dichloro-4-methylphenoxyacetate, 2,6-dichloro-4-(1,1,3,3-tetramethylbutyl)phenoxyacetate, 2,4-bis(1,1-dimethylpropyl)phenoxyacetate, chlorodiphenylacetate, isobutyrate, monosuccinoate, (E)-2-methyl-2-butenoate, o-(methoxycarbonyl)benzoate, α-naphthoate, nitrate, alkyl N,N,N',N'-tetramethylphosphorodiamidate, alkyl N-phenylcarbamate, borate, dimethylphosphinothioyl, alkyl 2,4-dinitrophenylsulfenate, sulfate, methanesulfonate(mesylate), benzylsulfonate, and tosylate (Ts). Methods of protecting and deprotecting hydroxyl groups, are well known and, for example, can be found in Protective Groups in Organic Synthesis (T. Green and P. Wuts; 3rd Edition; John Wiley and Sons, 1999).

A bond identified by " ------ " is either present or absent.

A bond identified by "∿∿∿" is one that includes a mixture of stereochemistries. ∿∿∿

The term "enantiomers" refers to stereoisomers of a compound that are mirror images of each other that are non-superimposable. In the application, unless otherwise mentioned or indicated, the chemical designation of compounds denotes the mixture of all possible stereochemically isomeric forms.

The term "diastereomers" refers to stereoisomers of a compound that have different configurations at one or more stereocenters but are not mirror images of each other (and therefore not enantiomers).

The term "epimers" refers to two diastereomers that differ from each other at only one stereocenter.

The term "alkyl" denotes a straight or branched hydrocarbon chain containing 1-12 carbon atoms, e.g., 1-6 or 1-4 carbon atoms. Examples of alkyl groups include methyl, ethyl, propyl, isopropyl, butyl, isobutyl, tert-butyl, and the like.

The term "aryl" refers to an aromatic 5-8 membered monocyclic or 8-12 membered bicyclic ring system. The term also includes aromatic bicyclic ring systems in which a hydrogen atom has been added to one, two, or three of the ring carbons in one of the rings (e.g., a partially saturated ring). Examples of aryl groups include phenyl, naphthyl and the like.

The term "acyl" denotes an alkyl or aryl group linked to a carbonyl group. Examples of acyl groups include formyl, acetyl, propionyl, acrylyl, benzoyl, and the like.

The term "benzoyl," as used herein, refers to the acyl of benzoic acid (attached through the carbonyl carbon) and has the following structure.

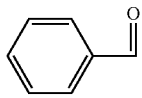

Compounds

One aspect of the invention relates to intermediate compounds useful for the synthesis of 2'-deoxy-2',2'-difluoro-tetrahydrouridine compounds.

In one aspect, the invention relates to a compound of Formula I:

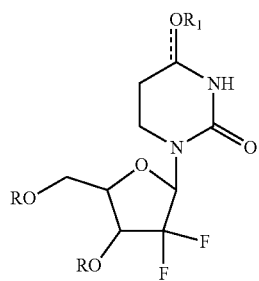

wherein R is a hydroxyl protecting group;
$R_1$ is H, a hydroxyl protecting group, or absent;
----- is a bond or absent; and
----- is absent when $R_1$ is H or a hydroxyl protecting group;
or a salt, or enantiomer, or diastereomer thereof. In certain embodiments, R is benzoyl. In other embodiments, R is benzoyl or TBDMS. In certain embodiments, $R_1$ is H or absent.

In some embodiments, the compound of Formula I has the structure of Formula Ia:

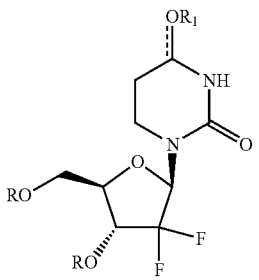

or a salt, or enantiomer, or diastereomer thereof. In certain embodiments, $R_1$ is H or absent.

In some embodiments, the compound of Formula I has the structure of Formula II:

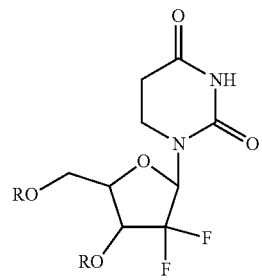

or a salt, or enantiomer, or diastereomer thereof. In certain embodiments, R is benzoyl.

In some embodiments, the compound of Formula I has the structure of Formula IIa:

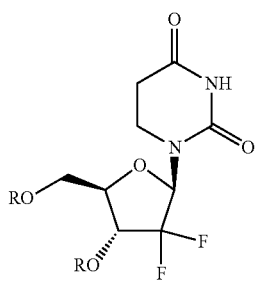

or a salt thereof.

In some embodiments, the compound of Formula I has the structure of Formula III:

III

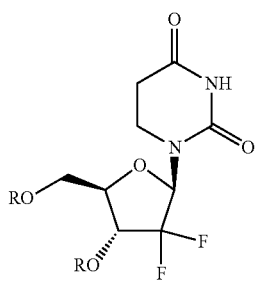

or a salt, or enantiomer, or diastereomer thereof. In certain embodiments, R is benzoyl.

In some embodiments, the compound of Formula I has the structure of Formula IIIa:

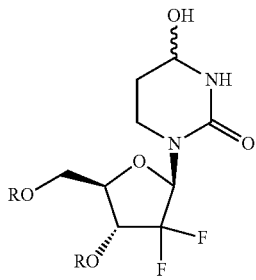

IIIa or a salt thereof.

In some embodiments, the compound of Formula I is compound 3:

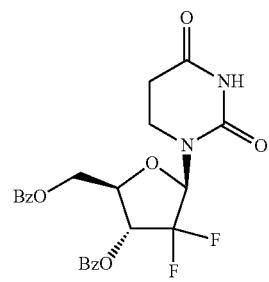

3 or a salt thereof, wherein Bz is benzoyl.

In some embodiments, the compound of Formula I is compound 4:

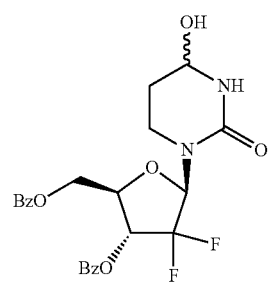

4 or a salt thereof, wherein Bz is benzoyl.

In one aspect, the invention relates to a compound of Formula V:

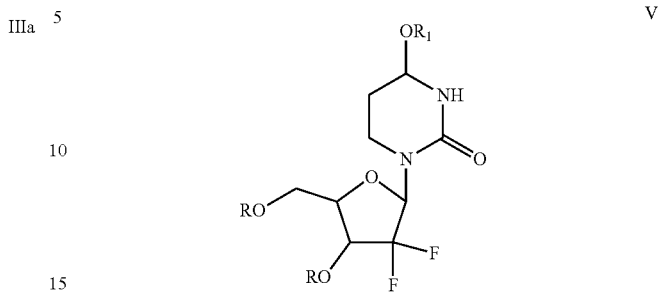

V wherein R and $R_1$ are independently hydroxyl protecting groups; or a salt, or enantiomer, or diastereomer thereof. In some embodiments, $R_1$ is an alkyl or acyl group. In some embodiments, $R_1$ is a $C_{1-12}$ alkyl group, e.g., a $C_{1-6}$ alkyl group, e.g., a $C_{1-4}$ alkyl group. In some embodiments, $R_1$ is a $C_{1-12}$ acyl group, e.g., a $C_{1-6}$ acyl group, e.g., a $C_{1-4}$ acyl group.

In some embodiments, the compound of Formula V has the structure of Formula Va:

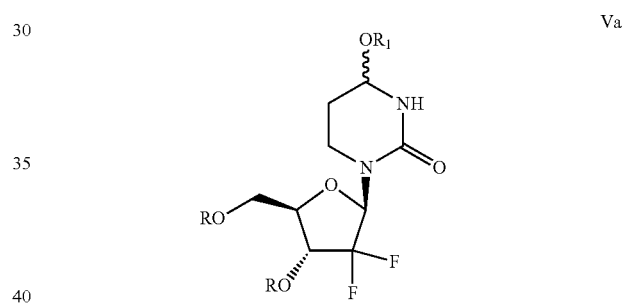

Va wherein R and $R_1$ are independently hydroxyl protecting groups;

or a salt, or enantiomer, or diastereomer thereof.

In some embodiments, the compound of Formula V has the structure of Formula Vb:

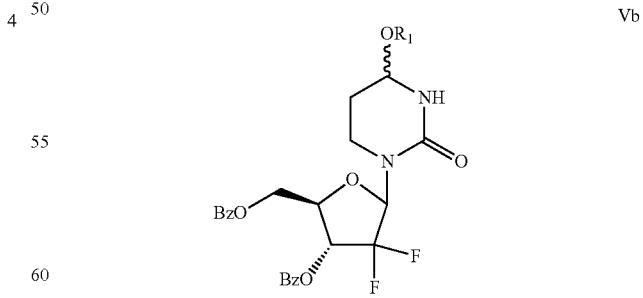

Vb wherein Bz is benzoyl and $R_1$ is a hydroxyl protecting group; or a salt, or enantiomer, or diastereomer thereof.

Certain of the compounds described herein contain one or more chiral centers, or may otherwise be capable of existing as multiple stereoisomers. The scope of the present invention includes pure stereoisomers as well as mixtures of stereoisomers, such as purified enantiomers/diastereomers/epimers, enantiomerically/diastereomerically/epimerically enriched mixtures, or racemates. In some embodiments, the compounds have a stereochemical purity of at least about 80%, e.g., at least about 85%, 90%, 95%, 96%, 97%, 98%, 99%, or more.

The compounds of the invention can also exist as tautomeric isomers, e.g., amide/iminol tautomers, in certain cases. Although only one delocalized resonance structure may be depicted, all such forms are contemplated within the scope of the invention.

The compounds disclosed herein can, as noted above, be prepared in the form of their pharmaceutically acceptable salts. Pharmaceutically acceptable salts are salts that retain the desired biological activity of the parent compound and do not impart undesired toxicological effects. Examples of such salts are (a) acid addition salts formed with inorganic acids, for example hydrochloric acid, hydrobromic acid, sulfuric acid, phosphoric acid, nitric acid and the like; and salts formed with organic acids such as, for example, acetic acid, oxalic acid, tartaric acid, succinic acid, maleic acid, fumaric acid, gluconic acid, citric acid, malic acid, ascorbic acid, benzoic acid, tannic acid, palmitic acid, alginic acid, polyglutamic acid, naphthalenesulfonic acid, methanesulfonic acid, p-toluenesulfonic acid, naphthalenedisulfonic acid, polygalacturonic acid, and the like; (b) salts formed from elemental anions such as chlorine, bromine, and iodine, and (c) salts derived from bases, such as ammonium salts, alkali metal salts such as those of sodium and potassium, alkaline earth metal salts such as those of calcium and magnesium, and salts with organic bases such as dicyclohexylamine and N-methyl-D-glucamine. In one embodiment the compounds disclosed herein are prepared in the form of a free base.

It is also understood that the compositions herein comprise compounds and combinations with stoichiometric or non-stoichiometric amounts of water, as in hydrates, or other components, as in solvates.

In some embodiments, the compounds of the invention have a purity of at least about 80%, e.g., at least about 85%, 90%, 95%, 96%, 97%, 98%, 99%, or more. In some embodiments, the compounds of the invention contain less than about 20%, e.g., less than about 15%, 10%, 5%, 4%, 3%, 2%, 1%, or 0.1% of impurities, reaction side products and/or degradation products.

One aspect of the invention relates to compound 1 (or salt thereof) produced by the methods of the present invention, in particular compound 1 in free base form having high purity (for example epimeric purity or low amounts of impurities, solvents, reaction side products and/or degradation products). Another aspect of the invention relates to compound 1 having a purity of at least about 80%, e.g., at least about 85%, 90%, 95%, 96%, 97%, 98%, 99%, 99.5%, or 99.9%, or more. In some embodiments, compound 1 contains less than about 20%, e.g., less than about 15%, 10%, 5%, 4%, 3%, 2%, 1%, or 0.1% of impurities, solvents, reaction side products and/or degradation products. A further aspect of the invention relates to compound 1 having a molar ratio of the desired epimer (compound 1) to the other epimer (compound 6) of at least about 60:40, e.g., at least about 70:30, 80:20, 90:10, 95:5, 96:4, 97:3, 98:2, 99:1 or more, e.g., an epimeric purity of at least about 60%, e.g., at least about 70%, 80%, 90%, 95%, 96%, 97%, 98%, 99%, or more, e.g., 99.5% or 99.9%.

Synthetic Methods

A further aspect of the invention relates to a method of producing compound 1:

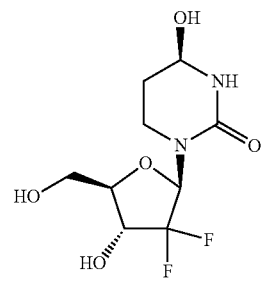

or a salt thereof;
comprising precipitating or crystallizing compound 1 from a solution of compound 2:

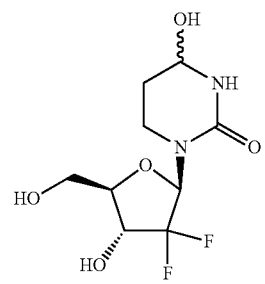

in the presence of a catalyst. In one embodiment, the method produces compound 1.

The method takes advantage of crystallization-induced diastereoselective transformation (CIDT) to provide enhanced production of the desired epimer (compound 1). Any suitable catalyst can be used in the method. The term "catalyst" as used herein with respect to the precipitation or crystallization step, refers to a compound that when present in sub-stoichiometric quantities relative to compound 2 promotes equilibration between compound 6 and compound 1. Without being limited by mechanism, it is believed that compound 1 and its epimer compound 6 are in equilibrium with an open aldehyde structure of the compound as an intermediate. The catalyst is thought to act by facilitating the opening of compound 6 to the aldehyde form, thereby increasing conversion of one epimer to the other and equilibrating the amount of compound 1 and compound 6 in solution as, upon usage of an appropriate solvent, compound 1 preferentially precipitates or crystallizes out of solution. The catalyst is present in a catalytically effective amount. In some embodiments, the catalyst can be an acid, e.g., an inorganic acid, e.g., an organic acid, e.g., acetic acid or trifluoroacetic acid. In other embodiments, the catalyst can be a base, e.g., a Bronsted-Lowry base, e.g., a weak base (one that does not ionize fully in an aqueous solution). In other embodiments, the catalyst can be diisopropylethylamine or ammonium hydroxide. In some embodiments, the base has a basicity of 10 or more in a solvent. In some embodiments, the base has a pKa of 10 or more in a solvent, e.g., DMSO, for example as reported in Bordwell, *Acc. Chem. Res.* 21:456 1988); Crampton, *J. Chem. Res.* (S) 22

(1997); Kaliurand et al., *J. Org. Chem.* 65(19):6202 (2000); Kaljurand et al, *J. Org. Chem.* 70(3):1019 (2005). In some embodiments, the catalyst is a strong base. In some embodiments, the catalyst is a strong base such as a sterically hindered strong base, e.g., a strong base which is a poor nucleophile. In some embodiments, the catalyst is 1,8-diazabicyclo(5.4.0)undec-7-ene (DBU). The DBU may be present in any amount that is effective, e.g., about 1 mol % to about 20 mol %, e.g., about 2 mol % to about 15 mol %, e.g., about 5 mol % to 10 mol %, e.g., about 5 mol %, or e.g., about 10 mol %, e.g., about 1, 2, 3, 4, 5, 6, 7, 8, 9, 10, 11, 12, 13, 14, 15, 16, 17, 18, 19, or 20 mol %. In some embodiments, the DBU may be present at 1 mol % to 20 mol %, e.g., 2 mol % to 15 mol %, e.g., 5 mol % to 10 mol %, e.g., 5 mol %, or e.g., 10 mol %, e.g., 1, 2, 3, 4, 5, 6, 7, 8, 9, 10, 11, 12, 13, 14, 15, 16, 17, 18, 19, or 20 mol %.

Any solvent or combination of solvents can be used that causes preferential precipitation or crystallization of compound 1 over compound 6. In one embodiment, the solvent is a solvent in which compound 6 has greater solubility than compound 1. In some embodiments, the solution used to form the solution of compound 2 comprises, consists essentially of, or consists of an organic solvent. In some embodiments, the solution comprises, consists essentially of, or consists of water or an aqueous solvent. In some embodiments, the solvent is a protic solvent. In some embodiments the solvent is one that is miscible with water. In particular embodiments, the solution is acetonitrile, acetone, tetrahydrofuran, dimethylsulfoxide, or methanol. In particular embodiments, the solution is aqueous acetonitrile, aqueous acetone, aqueous tetrahydrofuran, aqueous dimethylsulfoxide, or aqueous methanol. In a particular embodiment, the solution is aqueous acetonitrile.

The precipitation or crystallization can be carried out for a length of time sufficient for a suitable amount of compound 1 to be formed, e.g., about 0.5 days to 14 days, e.g., about 1-4 days, e.g., about 2-3 days, e.g., about 3-10 days, e.g., about 4-6 days. The precipitation or crystallization can be carried out at any suitable temperature, e.g., at about room temperature. After precipitation or crystallization is complete the precipitate can be collected, e.g., by filtration, and washed, e.g., with aqueous acetonitrile and/or acetonitrile. The progress of the reaction can be monitored, e.g., by sampling the supernatant of the reaction mixture and determining the ratio of compound 1 to compound 6. Completion of the reaction is indicated by the presence of a 50:50 mixture of compound 1 and compound 6 in the supernatant. If this ratio has not been achieved, additional catalyst can be added and the reaction continued until completion.

Following precipitation or crystallization, compound 1 optionally is further purified by recrystallization or slurrification, e.g., from aqueous acetonitrile, optionally with addition of an acid, e.g., trifluoroacetic acid. For example, the precipitate can be resuspended in water:acetonitrile in a ratio of about 1:2 to about 1:10 (v/v), heated to about 35-45° C., then cooled to about 0° C. The resulting precipitate can be washed in water:acetonitrile in a ratio of about 1:2 to about 1:10 (v/v) and then acetonitrile. In certain embodiments, compound 1 optionally is further purified by other methods known in the art, such as HPLC.

The molar ratio of the desired epimer (compound 1) to the other epimer (compound 6) after precipitation or crystallization can be at least about 60:40, e.g., at least about 70:30, 80:20, or 90:10 or more. The molar ratio of the desired epimer (compound 1) to the other epimer (compound 6) after a second purification step (e.g., recrystallization or slurrification) can be at least about 80:20, e.g., at least about 90:10, 95:5, or 98:2 or more. The purity of compound 1 can be increased by reduction in particle size. The particle size of compound 1 can be reduced for example by using manual means such as pestle and mortar or by mechanical means such as milling. This enables efficient release of excess solvent (for example acetonitrile). The efficacy of milling as a means to remove solvent was greater when the mill pressure was set to higher levels to allow for reduction of the particle size (D90) to about 50 µm or less, for example about m or less, in particular about 10 µm or less (e.g., between 0.1-10 µm, 1-10 µm, 1-25 µm or 1-50 µm). The process of air-jet milling the material mechanically allows the solvent to be released without re-slurrying. However, optional solvent re-slurry can also be performed subsequently for example by re-slurrying the material in ethyl acetate.

Another aspect of the invention relates to a method of producing compound 1:

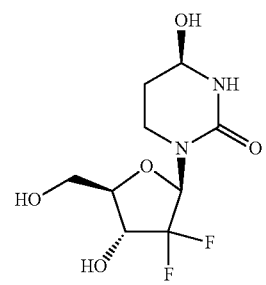

or a salt thereof;

comprising the steps of:

(a) hydrogenating the starting compound of Formula IV:

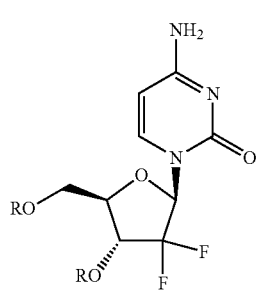

wherein R is a hydroxyl protecting group, to produce the compound of Formula IIa:

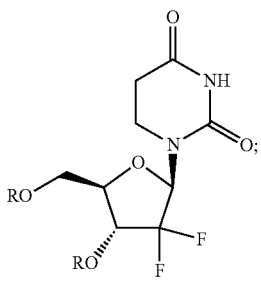

(b) reducing the compound of Formula IIa to produce the compound of Formula IIIa:

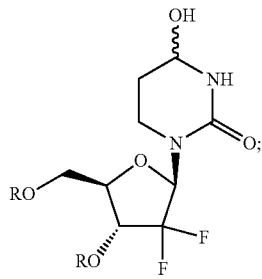

IIIa (c) deprotecting the compound of Formula IIIa to produce compound 2:

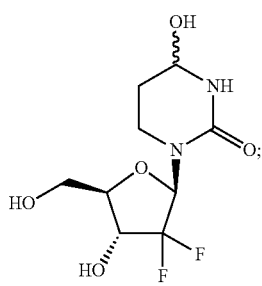

2 and
(d) precipitating or crystallizing compound 2 in the presence of a catalyst to produce compound 1:

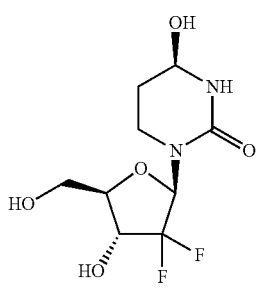

1 or a salt thereof.

The starting compound of Formula IV can be obtained commercially, e.g., from Aurora Fine Chemicals (San Diego, Calif.), or synthesized by known methods, for example as disclosed in Wheeler et al., J. Labeled Compounds Radiopharm. 29:583 (1991) and Chou et al., Synthesis 6:565 (1992), incorporated by reference herein in their entirety. The hydrogenation of the compound of Formula IV in step (a) to produce the compound of Formula IIa can be carried out by methods known in the art. For example, the step can be carried out under catalytic transfer hydrogenation conditions, e.g., in the presence of 5% palladium on charcoal. The hydrogenation can occur by heating the compound of Formula IV to reflux, e.g., with formic acid and hydrochloric acid in a solvent, e.g., aqueous ethyl acetate. Hydrogenation can be carried out at a temperature of about 50° C. to about 80° C., e.g., at about 68° C. for about 12-48 hours, e.g., about 24 hours. The reagents used to affect hydrogenation (e.g., palladium and charcoal) can be added after the reaction mixture is brought to the elevated temperature (e.g., about 50° C. to about 80° C., or, at about 68° C.). After completion, the catalyst can be removed, e.g., by filtering, and washed, e.g., with ethyl acetate. After separation of the organic layer it can be washed, e.g., with aqueous sodium bicarbonate and/or aqueous NaCl.

The reduction of the compound of Formula IIa to the compound of Formula IIIa in step (b) can be carried out by methods known in the art. For example, reduction can be carried out with a reducing agent such a sodium borohydride in an organic solvent, e.g., a mixture of methylene chloride and ethanol. The reduction can be carried out at any suitable temperature, e.g., around −5° C. to about 10° C., e.g., about 0° C. to about 5° C., for about 0.5 to 3 hours, e.g., about 1.5 hours. The reduction can optionally be carried out in the presence of cerium trichloride. In one embodiment, the amount of cerium chloride is about 50 mol % (e.g., 50 mol %). In another embodiment, the amount of cerium chloride is about 20 mol % or about 10 mol % (for example 20 mol % or 10 mol %). Following the reduction, the reaction can be quenched, e.g., with acetone, and the solution neutralized with an acid, e.g., hydrochloric acid. The organic layer containing the compound of Formula IIIa can be separated and washed, e.g., with water.

The deprotection of the compound of Formula IIIA to produce compound 2 in step (c) can be carried out by methods known in the art. For example, deprotection can be carried out in the presence of a weak base, e.g., ammonium hydroxide, in a solvent, e.g., methanol. The deprotection can be carried out for about 12-48 hours, e.g., about 24 hours. Following deprotection, the mixture can be concentrated, dissolved in an aqueous solvent, e.g., water, and washed with an organic solvent, e.g., ethyl acetate.

The precipitation or crystallization of compound 2 to produce compound 1 in step (d) can be carried out as described above.

In certain embodiments, the method can be modified to include a step of protecting the hydroxyl group of the compound of Formula IIIa to produce a compound of Formula Va, e.g., as part of step (b) above or as step (b1) after step (b). In one example, the method comprises the step of protecting the compound of Formula IIIa to produce a compound of Formula Va:

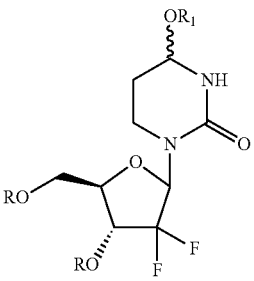

Va wherein R and $R_1$ are each independently a hydroxyl protecting group;
or a salt thereof.

In some embodiments, the method can further include the step of deprotecting the compound of Formula Va by removing the $R_1$ hydroxyl protecting group to produce the compound of Formula IIIa, e.g., as part of step (b) above or as step (b2) after steps (b) and (b). In other embodiments, the method can further include the step of deprotecting the compound of Formula Va by removing all of the hydroxyl protecting groups to produce compound 2, e.g., as an alternate step (c) or as step (b2) after steps (b) and (b1).

The protection of the compound of Formula IIIa to produce the compound of Formula Va can be carried out by methods known in the art. For example, the hydroxyl group can be protected as an ether. Protection of the hydroxyl group as an alkyl ether (e.g., a methyl ether) can be carried out with an alkylating agent (e.g., a methylating agent such as dimethyl sulfate) in the presence of, e.g., tetrabutylammonium iodide in a two-phase system, e.g., a mixture of hexanes and 50% aqueous sodium hydroxide. The reaction can be carried out at any suitable temperature, e.g., around 5° C. to about 45° C., e.g., about 30° C. to about 45° C., for about 0.5 to 6 hours, e.g., about 3 hours. Alternatively, the hydroxyl group can be protected as an ester. Protection of the hydroxyl group as an ester can be carried out with an acylating agent such as acetic anhydride in an organic solvent, e.g., pyridine. The acylation can be carried out at any suitable temperature, e.g., around 0° C. to about 40° C., e.g., about 15° C. to about 25° C., for about 8 to 24 hours, e.g., about 12 hours.

The deprotection of the compound of Formula Va where the hydroxyl group is protected as an ether to produce the compound of Formula IIIa can be carried out by methods known in the art. For example, cleavage of a methyl ether can be carried out with a Lewis acid such as boron trichloride in an organic solvent such as dichloromethane. The reaction can be carried out at any suitable temperature e.g., around −78° C. to about −65° C., for about 8 to 16 hours, e.g., about 12 hours.

The deprotection of the compound of Formula Va when the hydroxyl group is protected as an ester to produce compound 2 can be carried out by methods known in the art. For example, deprotection can be carried out in the presence of a weak base, e.g., ammonium hydroxide, in a solvent, e.g., methanol. The deprotection can be carried out for about 12-48 hours, e.g., about 24 hours. Following deprotection, the mixture can be concentrated, dissolved in an aqueous solvent, e.g., water, and washed with an organic solvent, e.g., ethyl acetate.

Uses

Compound 1 or a pharmaceutically acceptable salt thereof produced by the present invention can be used to inhibit CDA activity. Compound 1 or a pharmaceutically acceptable salt thereof can be in the form of a pharmaceutical composition, e.g., together with a pharmaceutically acceptable excipient. In some embodiments, compound 1 or a pharmaceutically acceptable salt thereof may be used in a method for treating cancer in a subject in need thereof in combination with a CDA substrate drug, e.g., a CDA substrate drug that may be used to treat cancer. Examples of CDA substrate drugs include, without limitation, decitabine, 5-azacytidine, gemcitabine, ara-C, tezacitabine, 5-fluoro-2'-deoxycytidine, and cytochlor. In some embodiments, the cancer may be selected from the group consisting of hematological cancers and solid cancers. In certain embodiments, the hematological cancer may be myelodysplastic syndromes or leukemia, e.g., acute myeloid leukemia or chronic myeloid leukemia. In certain embodiments, the solid cancer may be pancreatic cancer, ovarian cancer, peritoneal cancer, non small cell lung cancer, metastatic breast cancer, bladder cancer, squamous cell carcinoma, transitional cell carcinoma, adenocarcinoma, gynecological cancer, fallopian tube carcinoma, liver cancer, hepatocellular carcinoma, lung cancer, cervical carcinoma, genitourinary tract cancer, or gastrointestinal cancer. In some embodiments, compound 1 or a pharmaceutically acceptable salt thereof may be administered at substantially the same time with the CDA substrate drug, prior to the CDA substrate drug or after the CDA substrate drug, optionally in a single unit dosage form or in multiple, separate unit dosage forms.

Embodiments according to the present invention are described in non-limiting examples below.

Example 1

Preparation of Compound 4 from Compound 3

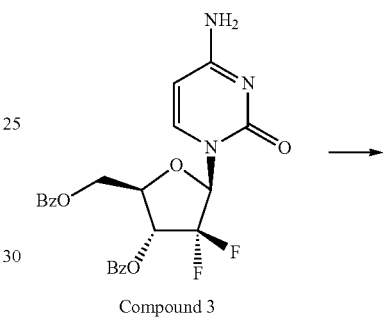

Compound 3

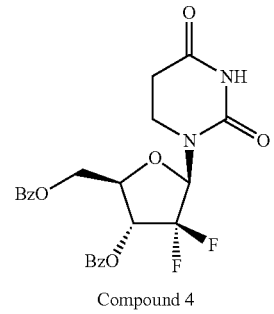

Compound 4

A mixture of compound 3 (300 g, 636 mmol), ethyl acetate (4.5 L), water (720 mL) and 1 N HCl (25.5 mL, 0.040 equiv) was stirred for 5 min and then charged with formic acid (240 mL, 10.0 equiv). After purging with nitrogen gas for 5 min, the mixture was heated to 68° C. and treated with Pd/C (120 g, 5 wt % dry basis, 50% wet, Degussa type E107 MA/W, 0.044 equiv). Stirring was continued at 68-70° C. for 24 h. The mixture was cooled to 30-35° C., filtered through a Celite® pad (300 g) and the pad was washed with ethyl acetate (1500 mL). The organic layer was separated from the filtrate, and washed three times with 10% aqueous NaHCO$_3$ (1500 mL) and then with 27% aqueous NaCl (750 mL). The organic layer was concentrated under reduced pressure to give crude compound 4 (290 g, 97% yield).

Example 2

Preparation of Compound 5 from Compound 4

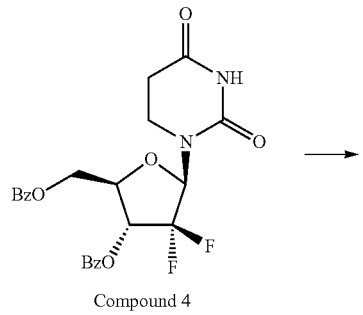
Compound 4

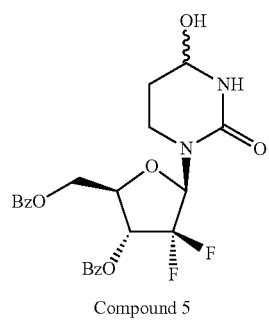
Compound 5

Compound 4 (99.3 g, 209 mmol) was dissolved in methylene chloride (1.1 L) and then treated with ethanol (0.73 L) and cerium (III) chloride heptahydrate (39 g, 105 mmol, 0.50 equiv). The mixture was agitated for 5 min and cooled down to 3° C. A solution of sodium borohydride (19.8 g, 523 mmol, 2.5 equiv) in water (94 mL) was added over 30 min maintaining the temperature below 6° C. The resulting mixture was stirred at 0° C. for 1.5 h. The reaction was quenched with acetone (42 mL, 565 mmol, 2.7 equiv) maintaining the temperature below 8° C. After stirring for 5 min, the mixture was treated with 0.2 M hydrogen chloride (1.2 L, 1.18 equiv) to adjust the pH to 7 maintaining the temperature below 8° C. The organic layer was separated at 2-10° C., mixed with 10% aqueous $NaHCO_3$ (0.44 L) and then warmed up to 25° C. The organic layer was separated, washed with water (0.33 L), and concentrated under reduced pressure to give a crude compound 5 (100.3 g).

Example 3

Preparation of Compound 2 from Compound 5

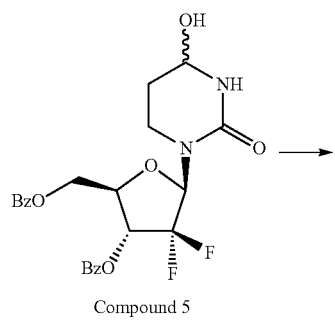
Compound 5

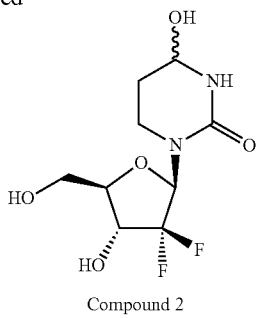
Compound 2

Compound 5 (90.4 g, 190 mmol) was treated with ammonia (7.0 M in methanol, 0.69 L, 25 equiv). The mixture was stirred at 25° C. for 27 h and then concentrated under reduced pressure. The residue was dissolved in water (570 mL) and washed twice with ethyl acetate (520 mL each). The aqueous layer was concentrated under reduced pressure at a temperature less than 35° C. to give compound 2 (48.5 g, 95% yield).

Example 4

Preparation of Compound 1 from Compound 2 Using DBU

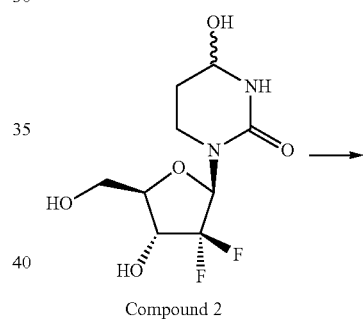
Compound 2

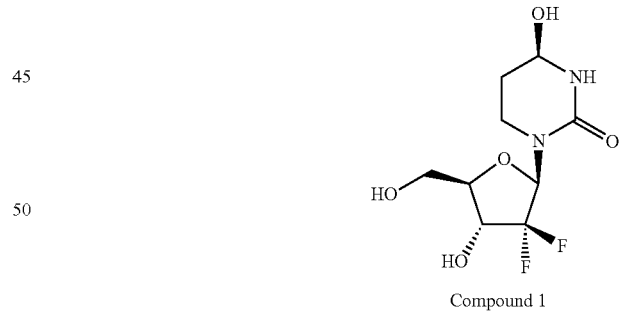
Compound 1

Compound 2 (164 g, 611.4 mmol, containing 25 mL of water by KF analysis) was suspended in a mixture of acetonitrile (39.2 mL) and water (40.7 mL). The mixture was stirred for 10 min to give a suspension of fine powder and treated with 1,8-diazabicyclo[5.4.0]undec-7-ene (9.1 mL, 61.0 mmol, 0.10 equiv). Stirring was continued at 25° C. for 64 h. The resulting precipitate was filtered, and washed with a 1:7 (v/v) mixture of water and acetonitrile (162 mL) and then twice with acetonitrile (164 mL each). The filter cake was dried over nitrogen purge to afford compound 1 (113.1 g, 69% yield; compound 1/compound 6 (epimer of compound 1)=90/10).

A portion of compound 1 (100 g, 372.8 mmol) was treated with acetonitrile (320 mL) and water (80 mL), and heated to 40° C. for 1.5 h. The mixture was then cooled to 0° C. over 4 h and stirred at 0° C. for 17 h. The precipitate was filtered and washed with a 1:6 (v/v) mixture of water and acetonitrile (100 mL) and then twice with acetonitrile (100 mL each). The filter cake was dried over nitrogen purge to afford compound 1 (86.1 g, 86.1% recovery; compound 1/compound 6 (epimer of compound 1)=95/5).

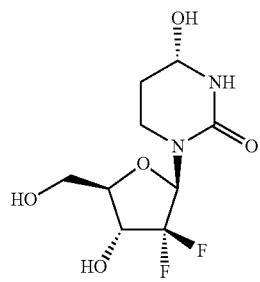

Compound 6

Example 5

Preparation of Compound 1 from Compound 2 Using DBU

An additional batch of compound 1 was prepared from compound 2 using DBU. Compound 2 (5.69 kg based on theoretical calculations of material prepared substantially as described in a scaled-up version of the examples above, 21.2 mol, containing 1.01 L of water by KF analysis) was suspended in a mixture of acetonitrile (19.4 L) and water (1.51 L). The mixture was stirred for 10 min to give a suspension of fine powder and treated with 1,8-diazabicyclo[5.4.0]undec-7-ene (150 g, 1.06 mol, 0.05 equiv). Stirring was continued at 25° C. for 2 h. A sample of the supernatant of the reaction mixture was submitted for HPLC to check if the supernatant solution was 50/50 compound 1/compound 6. The supernatant was a 50/50 mixture of compound 1/compound 6. No additional 1,8-diazabicyclo[5.4.0]undec-7-ene (150 g, 1.06 mol, 0.05 equiv was needed. The mixture was then stirred at 25° C. for 3 days. The resulting precipitate was filtered, and washed with a 1:7 (v/v) mixture of water and acetonitrile (4.3 kg) and then twice with acetonitrile (4.27 kg each). The filter cake was dried over nitrogen purge to afford compound 1 (3.53 kg, 59% yield; compound 1/compound 6=95/5).

A combined portion of compound 1 from the batch above and a second batch prepared in substantially the same manner (5.46 kg, 20.4 mol) was treated with acetonitrile (17.5 L) and water (4.4 L), and heated to 40° C. for 4 h. The mixture was then cooled to 0° C. over 4 h and stirred at 0° C. for 12 h. The precipitate was filtered and washed with a 1:6 (v/v) mixture of water and acetonitrile (4.5 kg) and then twice with acetonitrile (4.3 kg each). The filter cake was dried over nitrogen purge to afford compound 1 (3.97 kg, 73% recovery; compound 1/compound 6=98.6/1.4).

Example 6

Preparation of Compound 1 from Compound 2 Using Acetic Acid or Trifluoroacetic Acid

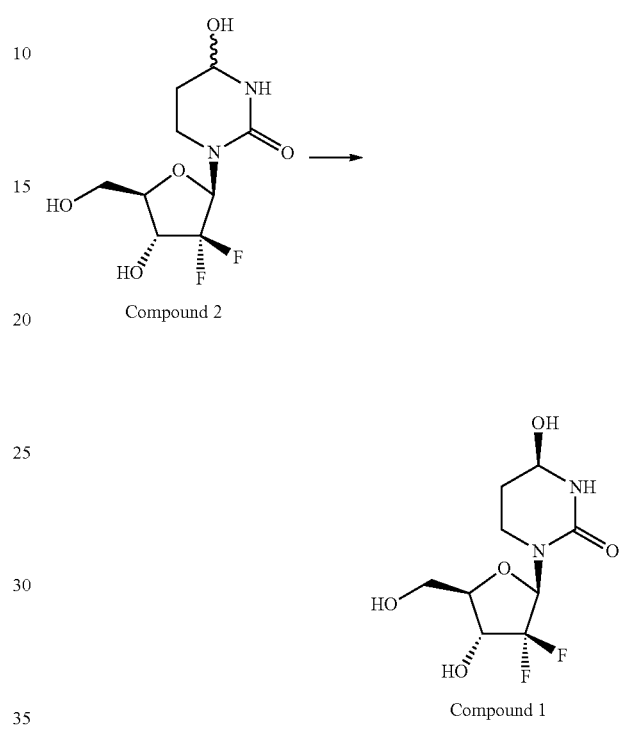

Compound 2

Compound 1

Compound 2 (45.8 g, 171 mmol) was treated with water (24 mL) and acetonitrile (163 mL) and stirred at ambient temperature for 10 min to give a suspension of fine powder. The mixture was treated with acetic acid (0.96 mL, 0.05 equiv) and stirred at 25° C. for 5 days. The resulting precipitate was filtered and washed with a 1:7 (v/v) mixture of water and acetonitrile (10.9 mL) and then twice with acetonitrile (16.4 mL each). The filter cake was dried over nitrogen purge to afford compound 1 (27.3 g, 60% yield; compound 1/compound 6 (epimer of compound 1)=93/7).

Compound 2 (48.6 g, 181 mmol) was suspended in a mixture of acetonitrile (84.0 mL) and water (25.8 mL) and heated to 80° C. for 5 min. The resulting solution was diluted with acetonitrile (90.0 mL) and cooled to 30° C. The mixture was treated with trifluoroacetic acid (0.14 mL, 1.81 mmol, 1.0 mol %) and stirred at ambient temperature for 4 days. The precipitate was filtered and washed with acetonitrile (25.0 mL) to give compound 1 (27.8 g, 57%, compound 1/compound 6 (epimer of compound 1)=95/5).

The foregoing is illustrative of the present invention, and is not to be construed as limiting thereof. The invention is defined by the following claims, with equivalents of the claims to be included therein.

All publications, patent applications, patents and other references cited herein are incorporated by reference in their entireties for the teachings relevant to the sentence and/or paragraph in which the reference is presented.

Column 25, Lines 55-65, Claim 1: Please delete Formula IIIa and replace with the following:
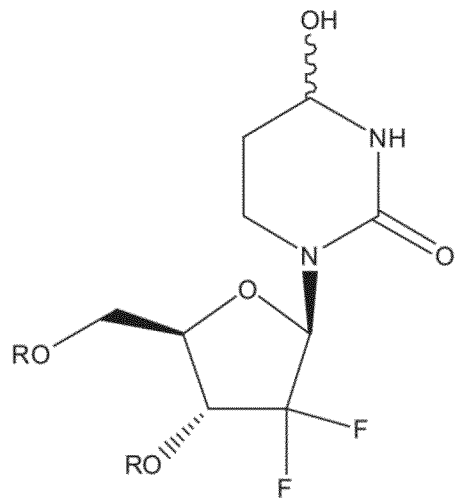

We claim:
1. A method of producing compound 1:

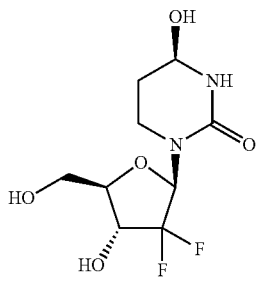

or a salt thereof;
comprising the steps of:
(a) hydrogenating the starting compound of Formula IV:

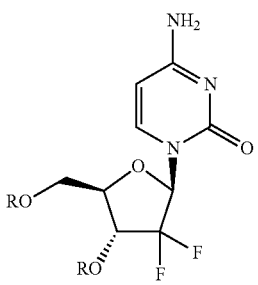

wherein R is a hydroxyl protecting group,
to produce the compound of Formula IIa:

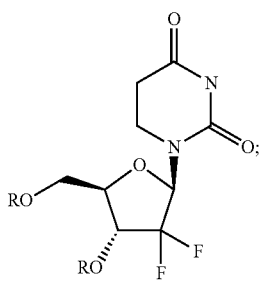

(b) reducing the compound of Formula IIa to produce the compound of Formula IIIa:

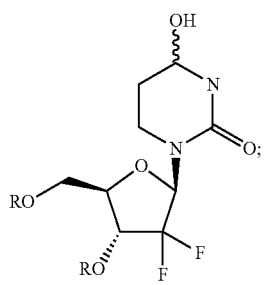

(c) deprotecting the compound of Formula IIIa to produce compound 2:

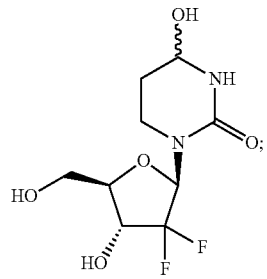

and
(d) precipitating or crystallizing compound 2 in the presence of a catalyst to produce compound 1:

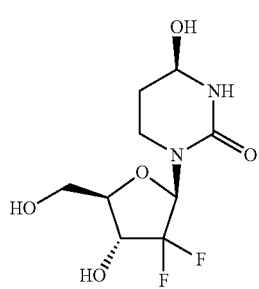

or a salt thereof;
wherein the catalyst is 1,8-diazabicyclo(5.4.0)undec-7-ene (DBU), acetic acid, trifluoroacetic acid, diisopropylethylamine, or ammonium hydroxide; and
wherein the hydrogenating in step (a) is carried out in the presence of a palladium catalyst.

2. The method of claim 1, wherein the catalyst is about 1 mol % to about 20 mol % DBU.

3. The method of claim 2, wherein the catalyst is about 5 mol % to about 10 mol % DBU.

4. The method of claim 3, wherein the catalyst is about 5 mol % DBU.

5. The method of claim 1, wherein the catalyst is acetic acid, trifluoroacetic acid, diisopropylethylamine, or ammonium hydroxide.

6. The method of claim 1, wherein the final product is recrystallized or slurrified.

7. The method of claim 1, wherein step (d) is carried out in the presence of a solution comprising acetonitrile.

8. The method of claim 1, wherein step (d) is carried out in the presence of a solution comprising acetone or tetrahydrofuran.

9. The method of claim 1, wherein step (b) is carried out in the presence of CeCl$_3$.

10. The method of claim 1, further comprising a step of reducing the particle size of compound 1.

11. The method of claim 10, wherein the particle size is reduced to about 50 μm or less.

12. The method of claim 1, wherein the palladium catalyst is palladium on charcoal.

* * * * *

UNITED STATES PATENT AND TRADEMARK OFFICE
CERTIFICATE OF CORRECTION

PATENT NO. : 11,028,119 B2
APPLICATION NO. : 16/717811
DATED : June 8, 2021
INVENTOR(S) : Choi et al.

It is certified that error appears in the above-identified patent and that said Letters Patent is hereby corrected as shown below:

In the Specification

Column 8, Line 46: Please remove "〰〰"

Column 16, Line 10: Please correct "m or less" to read -- 25 µm or less --

In the Claims

Column 25, Lines 38-50, Claim 1: Please delete Formula IIa and replace with the following:

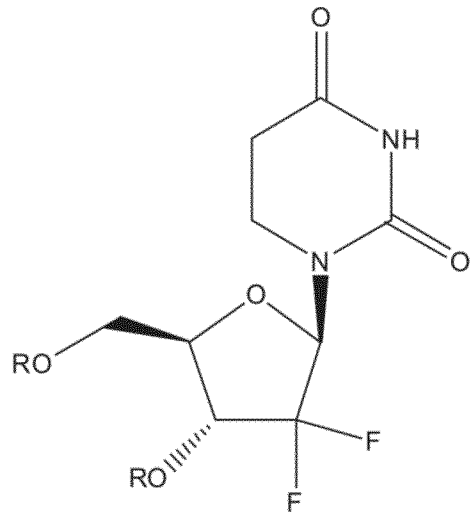

Signed and Sealed this
Fifth Day of October, 2021

Drew Hirshfeld
*Performing the Functions and Duties of the*
*Under Secretary of Commerce for Intellectual Property and*
*Director of the United States Patent and Trademark Office*